Figure 1:
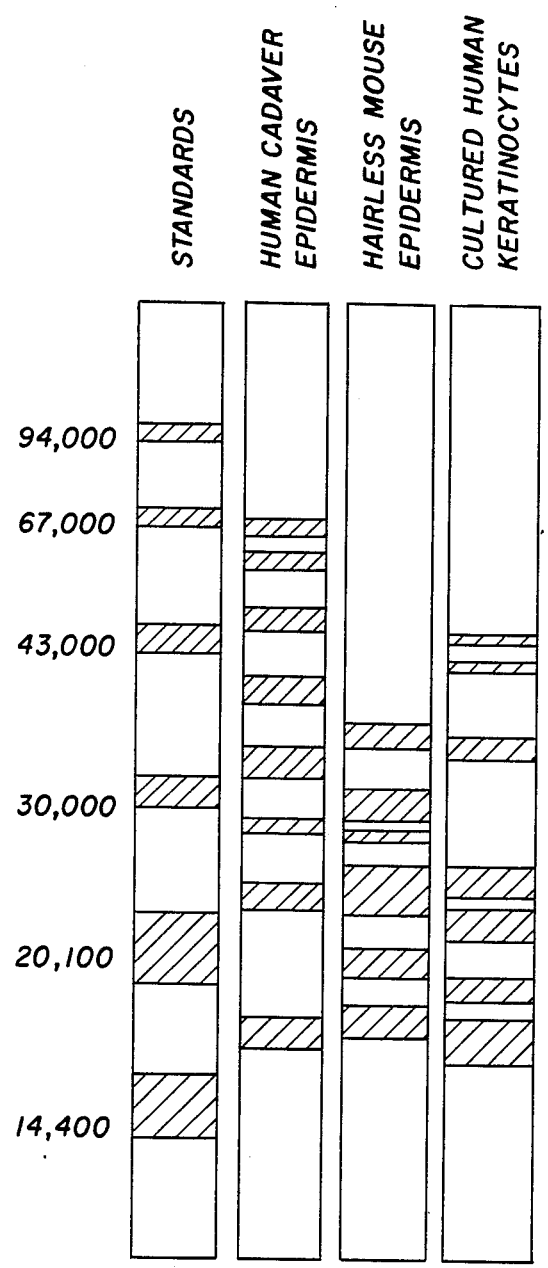

United States Patent [19]

Schiltz et al.

[11] Patent Number: 4,792,571
[45] Date of Patent: Dec. 20, 1988

[54] PROTEOLIPID COMPOUNDS

[75] Inventors: John R. Schiltz, Ramsey, N.J.; Peter M. Elias, Muir Beach, Calif.

[73] Assignee: American Cyanamid Company, Stamford, Conn.

[21] Appl. No.: 815,491

[22] Filed: Jan. 2, 1986

[51] Int. Cl.$^4$ .............. C07K 3/02; A61K 7/48; G01N 33/50; G01N 33/92

[52] U.S. Cl. .................. 514/773; 514/2; 514/21; 514/946; 514/947; 424/70

[58] Field of Search .......... 514/946, 947, 844, 845, 514/846, 847, 848, 21, 2, 773; 424/70

[56] References Cited

U.S. PATENT DOCUMENTS

| | | | | |
|---|---|---|---|---|
| 3,033,755 | 5/1962 | Jacobi | ............... | 514/21 X |
| 3,194,737 | 7/1965 | Jacobi | ............... | 514/21 X |
| 4,140,759 | 2/1979 | Mausner | ............... | 514/2 |
| 4,481,186 | 11/1984 | Deckner | ............... | 514/847 X |
| 4,578,384 | 3/1986 | Hollinger | ............... | 514/953 X |

FOREIGN PATENT DOCUMENTS 8501890 5/1985 Japan .................. 514/847

Primary Examiner—John F. Terapane
Assistant Examiner—John S. Maples, Jr.
Attorney, Agent, or Firm—Anthony M. Santini; Charles J. Fickey

[57] ABSTRACT

Certain proteolipid humectant macromolecules; method of obtaining by isolating these from tissue of vertebrates or by culturing; use of such proteolipids to treat dry human skin; compositions containing such proteolipids; and method for analysis of proteolipid concentration.

4 Claims, 4 Drawing Sheets

HUMAN SKIN MOISTURIZATION

SDS-PAGE OF PROTEOLIPIDS

CONCENTRATION EFFECTS OF BOVINE PROTEOLIPIDS ON SKIN MOISTURIZATION

HUMAN SKIN MOISTURIZATION

PROTEOLIPID COMPOUNDS

This invention relates to unique humectancy agents for personal care which are proteolipid compounds extracted from vertebrate tissue. Such proteolipids are useful for any topical application to promote water retention in mammalian skin, epidermal tissue and hair.

BRIEF DESCRIPTION OF THE INVENTION

We have established the existence of a class of unique amphiphatic proteolipid macromolecules in human, hairless mouse and bovine epidermis and cultured human skin epidermal cells whose natural function in the skin is to trap and hold water to the stratum corneum. Methods for isolating and purifying these naturally-occurring humectant macromolecules are described, and they have been characterized in terms of their molecular weights and amino acid and lipid compositions. The proteolipids absorbed up to 120 times their weight with water, and their moisturizing properties on human skin following topical application were demonstrated using electrical impedance measurements. Immunofluorescence and skin layering studies demonstrated that the proteolipids are present in human skin in the epidermal stratum granulosum and stratum corneum.

BACKGROUND OF THE INVENTION

The stratum corneum from animal skin arises as a result of a programmed differentiation of underlying epidermal keratinocytes. The terminal events involved in the formation of this non-living structure from living stratum granulosum cells are complex and the molecular mechanisms are incompletely understood. The process involves nuclear explusion, externalization of lipid-containing lamellar bodies, enzyme-catalyzed degradation and selective loss of all major classes of macromolecules and cellular dehydration. The dehydrated cells become flattened and they adhere tightly to form the final laminated structure which provides a selective barrier to the entry or exit of substances to or from the skin.

Numerous lines of investigation have led to the principle that the extent of hydration of the stratum corneum is responsible for the clinical feel and appearance of dry skin. The stratum corneum from normal skin contains 10–20% water, whereas the stratum corneum from clinically dry skin contains 5–10% water. Dry stratum corneum can be treated by direct addition of water, by occlusion to prevent water evaporation or by addition of substances with humectant (i.e. water-retaining) activity. Humectants commonly used in skin moisturizing products include glycerol, urea, propylene glycol, mineral oil and pyroolidine carboxyllic acid. More recently, naturally-occurring macromolecules such as collagen, hyaluronic acid, elastin or placental proteins have been used as humectants. Although all these substances are reasonably good humectants, it is clear that none of them are involved in the natural mechanisms of stratum corneum moisturization. We have identified and described a class of proteolipids from epidermis that represents at least one of the natural molecules whose function is to hydrate the stratum corneum. Proteolipids are ideally suited for this function. Because of their amphiphatic nature, the lipid portion of these "hybrid" molecules should bind to the hydrophobic stratum corneum, leaving the hydrophilic protein portion free to bind water.

A class of compounds, lipoproteins, is known. However compounds of this class differ from proteolipids in the following respect. Lipoproteins are a loose combination of a protein and a fatty acid held together by electrostatic attraction (such as a salt) and therefore the protein and lipid parts separate in aqueous solution. Proteolipids, on the other hand, consist of a protein and fatty acid joined by a covalent bond, the exact nature of which is not yet known. Thus the components of a proteolipid do not separate in aqueous solution and the proteolipid exists as such in water.

DESCRIPTION OF THE INVENTION

The following will outline in detail the methods we have used to isolate, purify and characterize a unique group of humectant proteolipid molecules from hairless mouse or human epidermis, cultured human skin epidermal cells and bovine snout epidermis. Their chemical characterization, tissue localization, humectant properties and moisturizing effects on human skin will be described.

The epidermis is first separated from the dermis. The epidermis is then submitted to a series of treatments to separate proteins, polysaccharides, nucleic acids, free polar lipids and free fatty acids to obtain pure proteolipid compounds. These proteolipid compounds are fat soluble and are then treated to convert them to water soluble compounds.

The process is defined in detail in the following specific examples:

EXAMPLES 1 TO 3

Proteolipid Extraction and Purification From Mouse, Human and Bovine Tissue

To isolate epidermis from hairless mice or human cadavers, full thickness skin pieces were placed dermis-down onto plastic petri dishes, which were floated on a 60° C. water bath for one minute. The epidermis was then removed by scraping with a scalpel. Epidermis from bovine snout was dissected from freshly slaughtered or frozen tissues. After washing with cold phosphate-buffered saline, the tissues were suspended in 5 volumes of ice-cold chloroform:methanol (1:1), and 0.01 volumes of 2M KCl was added. The tissue was homogenized on ice for 30 seconds and stirred at room temperature for 30 minutes. The homogenate was filtered through defatted Whatman #1 paper. The filtrate was centrifuged and the upper chloroform phase collected and concentrated to one-half the initial tissue volume by rotary evaporation. Five volumes of cold acetone were added and the solution was allowed to remain at −20° C. for 2 hours. After centrifugation in a refrigerated centrifuge, the precipitate was washed 3 times with 10 volumes of cold ethanol:ether (1:1). The pellet was suspended in one-half the original tissue volume of chloroform:methanol:HCl (15:15:0.1) and precipitated by the addition of 5 times the volume of acetone at −20° C. overnight. The precipitate was collected by centrifugation and suspended in one-half the original tissue volume of chloroform:methanol (1:1). In order to transfer the proteolipids to the water phase, the solution was placed at 37° C. and nitrogen was bubbled into the solution as water was slowly added in a dropwise fashion until cloudiness developed. Nitrogen bubbling was continued until the chloroform and methanol evaporated, at which time the solution clarified.

Proteolipid Molecular Weight Profiles

The purified proteolipid fraction as prepared above was subjected to molecular wegith analysis by sodium dodecyl sulfate-polyacrylamide gel electrophoresis (SDS-PAGE). As shown in FIG. 1, 4 to 6 distinct protein species were present, which ranged in molecular weight from 20,000 to 66,000 daltons. Although the profiles shown are from cultured human epidermal cells, human cadaver epidermis and hairless mouse skin, similar molecular weight distributions were observed in the proteolipids from bovine snout epidermis.

EXAMPLE 4

Proteolipid Amino Acid and Lipid Content

The amino acid composition of the proteolipid fraction from cultured human epidermal cells is shown in Table 1. Approximately half the residues are hydrophobic, and would be expected to insert into the lipid portion of the cell membrane. The remaining half are hydrophilic, and could bind water.

The lipid portion of the human proteolipid fraction was removed by treating the material overnight by acid methanolysis (5% HCL in methanol at 70° C.). The fatty acid methyl esters were then identified by gas chromatography (Table II). Unidentified components accounted for approximately 7% of the total lipids, which were not included in the calculations.

TABLE I

HUMAN EPIDERMAL PROTEOLIPID

| AMINO ACID | RESIDUES/1000 |
|---|---|
| HYDROPHOBIC | |
| Alanine | 91 |
| Leucine | 127 |
| Isoleucine | 54 |
| Valine | 56 |
| Proline | 56 |
| Phenylalanine | 62 |
| Tryptophane | 21 |
| Methionine | 31 |
| Total | 496 |
| MILDLY HYDROPHILIC | |
| Serine | 69 |
| Threonine | 61 |
| Tyrosine | 44 |
| Asparagine | N.D. |
| Glutamine | N.D. |
| Cysteine | 23 |
| Glycine | 87 |
| Total | 284 |
| VERY HYDROPHILIC | |
| Lysine | 36 |
| Arginine | 36 |
| Histidine | 18 |
| Aspartic Acid | 63 |
| Glutamic Acid | 65 |
| Total | 218 |

TABLE II

LIPID CONTENT OF HUMAN PROTEOLIPID FRACTION

| LIPID | % Of Total Lipid Wt. |
|---|---|
| C-16:0 | 37.0 |
| C-18:0 | 25.8 |
| C-18:1 | 15.3 |
| C-20:3 | 14.0 |
| Unidentified | 7.0 |

EXAMPLE 5

Proteolipid Localization in the Epidermis

The localization of proteolipids in human epidermis was determined using techniques of immunofluorescence and skin layering. The 20,000 molecular weight proteolipid species from cultured human epidermal cells was cut from slab SDS-PAGE gels, emulsified with Fruend's complete adjuvant and injected into rabbits and sheep. After appropriate times, the immune sera were collected and the indirect immunofluorescence stain technique was employed to localize the antigen in frozen sections of human skin. The 20,000 mol. wt. proteolipid localized primarily to the statum granulosum and stratum corneum. When hairless mouse skin was separated into different layers by trypsinization and examined by extraction, purification and weighing, it was determined that 63% of the total proteolipid was recovered in the stratum corneum, 29% in the stratum granulosum and 8% in the stratum basale (Table III).

TABLE III

PROTEOLIPID CONTENT OF VARIOUS LAYERS OF EPIDERMIS (From The Hairless Mouse)

| Epidermal Layer | Wet Weight Tissue (g) | Proteolipid Recovered (mg) | % of Wet Wt. | % of Total Proteolipid |
|---|---|---|---|---|
| Stratum corneum | 6.15 | 1.5 | 0.024 | 62.5 |
| Stratum granulosum | 1.14 | 0.7 | 0.061 | 29.2 |
| Stratum basale | 1.50 | 0.2 | 0.013 | 8.3 |

EXAMPLE 6

Humectantcy of Proteolipids

A sensitive radioactive assay procedure was developed to assess the water-absorbing (i.e. humectant) properties of proteolipids and other molecules. A solution or fine suspension of known amounts of the material to be assayed was placed in a scintillation vial and evaporated to dryness in a vacuum centrifuge at 45° C. The vials were then transferred onto a porcelain stand in a glass chamber containing $^3H-H_2O$ (100 $\mu$Ci/ml). The chamber was sealed and placed at 37° C. such that the relative humidity quickly equillibrated to 100%. After 20 hours the vials were removed, scintillation fluid was added and the radioactivity determined in a liquid scintillation counter. For determination of bound water, the amounts of proteolipids or other test substances were varied from 1-50 $\mu$g/vial (all in 1 ml solvent), samples and solvent controls were run in triplicate and the water bound/ug substance was calculated from the slope of the linear DPM/ug substance curve. The results (Table IV) are expressed as ug water bound/ug substance. For comparison, the values for other lipids, hyaluronic acid (a known humectant) and collagen are included. The proteolipids are clearly better humectants than free fatty acids, complex lipids (cerebrosides and ceramides), neutral lipids, hyaluronic acid or collagen.

TABLE IV

HUMECTANTCY OF VARIOUS SUBSTANCES

| SUBSTANCE | $\mu$g $H_2O$ Absorbed/$\mu$g Substance |
|---|---|
| Epidermal Proteolipids | |
| Murine | 119.8 |

TABLE IV-continued

| HUMECTANTCY OF VARIOUS SUBSTANCES | |
|---|---|
| SUBSTANCE | μg H$_2$O Absorbed/μg Substance |
| Bovine | 68.0 |
| Hyaluronic Acid | 19.7 |
| Collagen (Human, Native) | 2.0 |
| Lipids | |
| Neutral lipid mix (Cholesterol, triglycerides, sterol esters, free fatty acids) | 31.7 |
| Palmitic Acid | 9.9 |
| Stearic Acid | 3.3 |
| Cerebrosides | 0 |
| Ceramides | 0 |

EXAMPLE 7

Moisturizing Effects of Bovine Proteolipids on Human Skin

Figure 2:
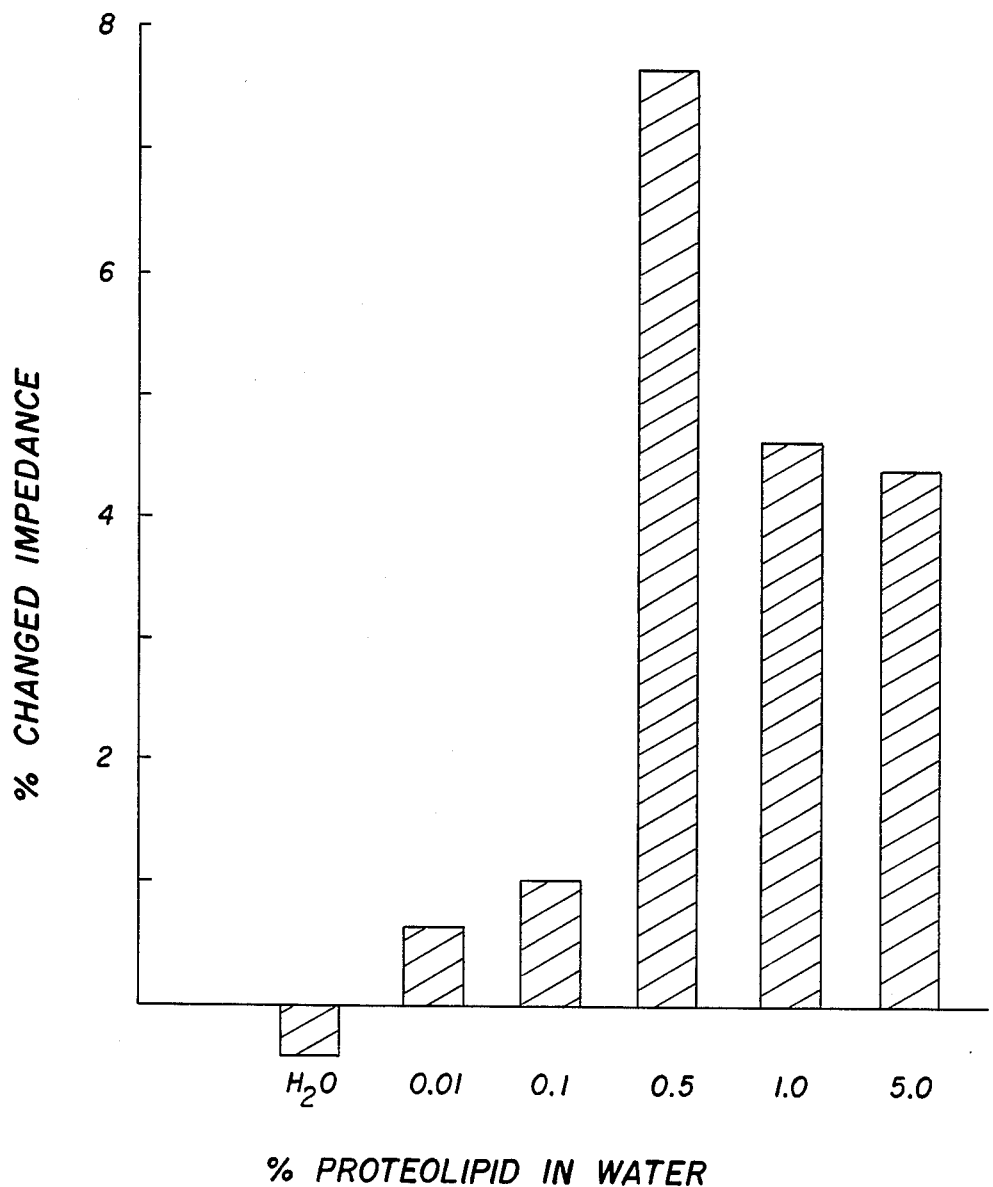
Figure 3:
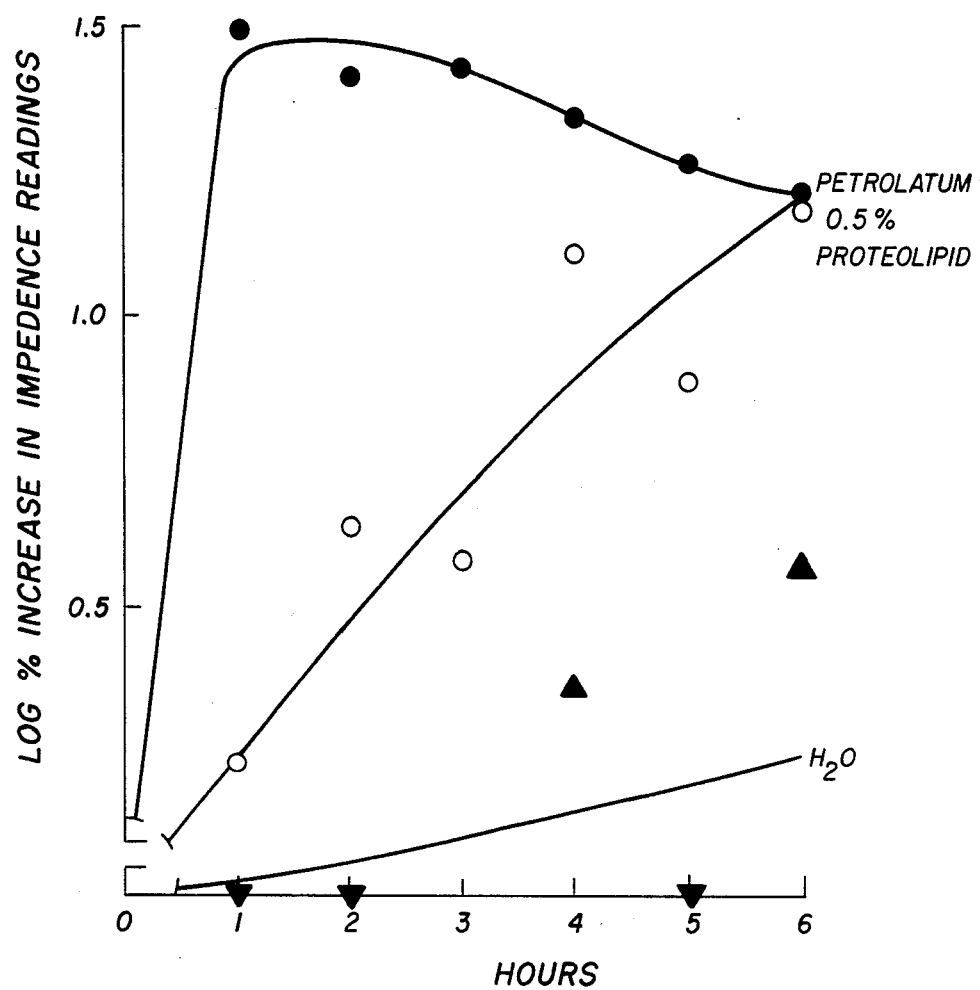

Electrical impedence measurements on 46 human female subjects were taken at hourly intervals during a 6-hour period following topical application of bovine proteolipids to their forearms. Treatment sites were randomized and each subject received all the different proteolipid solutions (0.001%, 0.01%, 0.1%, 0.5%, 1% and 5% in water), water alone or petrolatum. Baseline readings at each site were taken, the materials were applied and the data are expressed as % changes in readings over baseline during subsequent sampling periods. When the values were averaged over all six hours of the experiment, the proteolipids significantly increased the water content of the stratum corneum, compared to water alone, and the most effective concentration tested was 0.5% (FIG. 2). The kinetics of moisturization during the 6-hour period for water, 0.5% proteolipid or petrolatum is shown in FIG. 3. Compared to water, the proteolipids increased the rate of hydration of the stratum corneum, and the increase was statistically significant at the 95% confidence level (note: the water actually induced a decline in moisture after 1, 2 and 5 hours, but the data are plotted on the log plot as 0). The moisturizing effects of petrolatum were significantly greater than all other materials during the first 5 hours; at 6 hours it was not significantly different from the proteolipids. The data in FIG. 3 clearly demonstrates the different modes of action of petrolatum and proteolipids. Because of its occlusive properties, petrolatum induced a rapid increase in stratum corneum water content, but the effect declined throughout the 6-hour experiment. In contrast, the humectant proteolipids gradually increased the water content until at 6 hours water content was equivalent to petrolatum.

Figure 4:
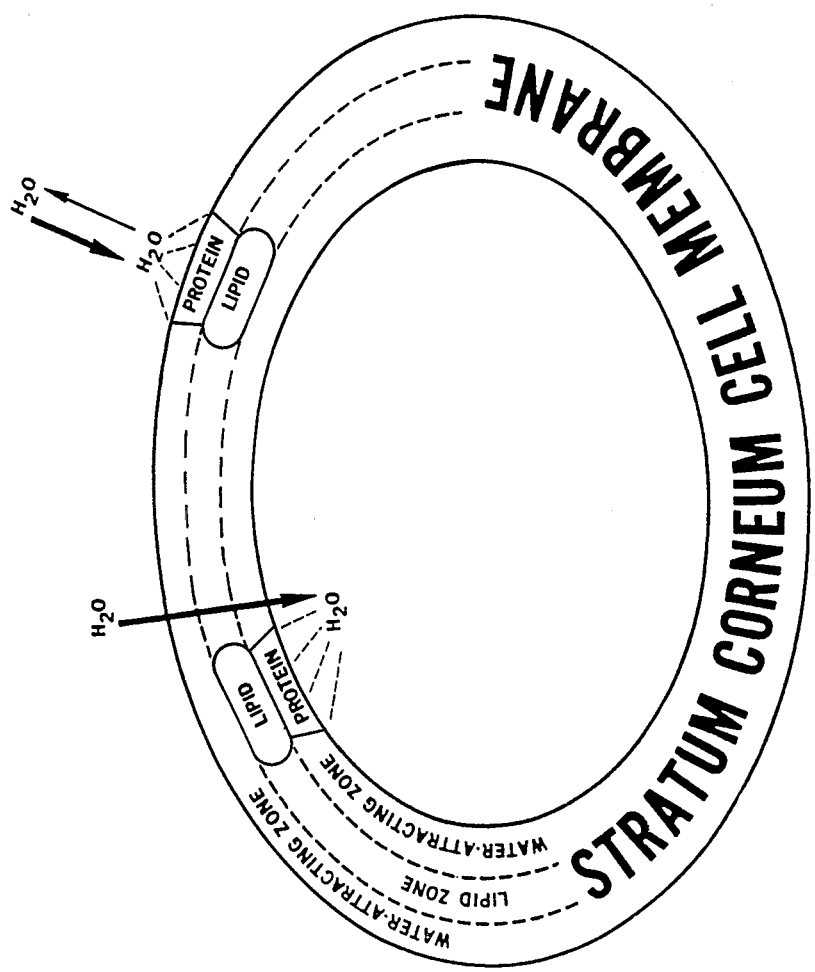

Our concept as to how proteolipids moisturize the stratum corneum is illustrated in FIG. 4. The diagram is of a single stratum corneum cell. It is well established that these cell membranes contain a hydrophobic lipid zone which is sandwiched between two hydrophilic water attracting zones. Both hydrophilic zones will preferentially bind water or other substances such as sugars or proteins, whereas the hydrophobic zone would preferentially bind lipids. The amphiphatic proteolipids would sit fixed in the membrane as shown and trap and hold water to the membrane. The water would arise from the bloodstream through the dermal circulation or from the atmosphere. The proteolipid would also exist bound to the inner surface of the cellular membrane; the net effect in this case is that water would accumulate within the cell and cause it to "puff up."

What is claimed is:

1. A method for enhancing the humectancy of mammalian skin, epidermal tissue and hair which comprises topically applying thereto an effective amount of at least one proteolipid compound.

2. The method of claim 1 wherein said proteolipid compound is applied as a composition containing from about 0.01 to 5 percent of said proteolipid compound.

3. The method of claim 1 wherein said proteolipid compound is extracted from vertebrate tissue.

4. The method of claim 1 which comprises applying a mixture of proteolipid compounds.

* * * * *